United States Patent [19]

Stapp

[11] 4,044,041
[45] Aug. 23, 1977

[54] PREPARATION OF ESTERS OF UNSATURATED ALCOHOLS

[75] Inventor: Paul R. Stapp, Bartlesville, Okla.

[73] Assignee: Phillips Petroleum Company, Bartlesville, Okla.

[21] Appl. No.: 624,694

[22] Filed: Oct. 22, 1975

[51] Int. Cl.$^2$ .............. C07C 67/04; C07C 121/52; C07C 121/54

[52] U.S. Cl. .............. 260/465 D; 260/408; 260/410; 260/410.5; 260/410.9 N; 260/464; 260/465.4; 260/468 R; 260/468 K; 260/469; 260/475 N; 260/476 R; 260/485 R; 260/485 H; 260/485 L; 260/485 N; 260/487; 260/491; 260/497 R

[58] Field of Search .......... 260/475 N, 476 R, 497 R, 260/410.9 N, 468 R, 468 K, 487, 410.5, 410, 491, 465 D, 465.4, 464, 408, 485 N, 485 L, 485 H

[56] References Cited

U.S. PATENT DOCUMENTS

| 3,595,905 | 7/1971 | Schlutz | 260/497 A |
| 3,723,510 | 3/1973 | Ono et al. | 260/497 R |
| 3,742,039 | 6/1973 | Ono et al. | 260/497 A |

FOREIGN PATENT DOCUMENTS

| 1,138,366 | 1/1969 | United Kingdom | 260/497 A |

OTHER PUBLICATIONS

Inagaki et al., C. A. 75, 129289$d$ (1971).

*Primary Examiner*—Jane S. Myers

[57] ABSTRACT

Esters of monounsaturated alcohols are prepared by reacting a carboxylic acid with a conjugated diene in the absence of oxygen, employing a catalyst system including copper ions, alkali metal ions, and halide ions.

23 Claims, No Drawings

PREPARATION OF ESTERS OF UNSATURATED ALCOHOLS

FIELD OF THE INVENTION

The invention relates to a process for the production of esters of monoolefinic alcohols.

BACKGROUND OF THE INVENTION

Esters of monoolefinically unsaturated alcohols are useful as monomers in polymerization systems to give a variety of resins, plastics, and the like. Needed have been methods to prepare such monomers by convenient and effective means.

BRIEF SUMMARY OF THE INVENTION

I have discovered a method of preparing esters of monoolefinically unsaturated alcohols with comprises reacting a carboxylic acid with a conjugated diene in the absence of oxygen while employing a catalyst system comprising copper ions, alkali metal ions, and halide ions.

DETAILED DESCRIPTION OF THE INVENTION

Conjugated Dienes

Conjugated diolefins employed in my process include the acyclic, as well as the cyclic types. The hydrocarbon conjugated dienes are preferred for convenience and availability. A wide variety of substituents can be on the conjugated diolefins since the reaction of the carboxylic acid with the conjugated diene occurs across one or both of the diene double bonds, and various substituents generally do not interfere in the reaction.

These conjugated dienes preferably contain up to 16 carbon atoms per molecule, and consequently the acyclic conjugated dienes will contain 4 to 16 carbon atoms per molecule, and the cyclic conjugated dienes 5 to 16 carbon atoms per molecule. This limitation is not based on operability, but simply is a matter of convenience and availability of reactants, since those of the carbon atom range indicated are more readily available.

The acyclic conjugated dienes also can be represented by the general formula:

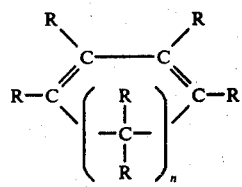

(I)

The cyclic conjugated diolefins also can be represented by the general formula:

(II)

In the conjugated diene formulas above, each R is individually selected from hydrogen, a halogen including fluorine, chlorine, bromine, or iodine, cyano,—COOR', and the monovalent hydrocarbyl radicals including alkyl, cycloalkyl, aryl, and combination radicals including such as alkaryl, aralkyl, cycloalkaryl, and the like. R' represents hydrogen, alkyl, or aryl radicals of up to 10 carbon atoms. The total number of carbon atoms in all substituents preferably should not exceed about 12 because of considerations of availability and reactivity. In the cyclic conjugated diene formula above, the integer indicator n has the value of preferably 1 to 12.

Exemplary conjugated diolefins include 1,3-butadiene, 2-methyl-1,3-butadiene, 2-chloro-1,3-butadiene, 2-ethyl-1,3-butadiene, 2-chloro-3-methyl-1,3-butadiene, 1,4-diphenyl-1,3-butadiene, 1,3-hexadiene, 1,3-pentadiene, 1,3-octadiene, 1,3-cyclohexadiene, 1,3-cyclooctadiene, 1,3-cyclododecadiene, 2-cyano-1,3-butadiene, -carbethoxy-1,3-butadiene, cyclopentadiene, 5-methyl-1,3-cyclohexadiene, 2,4-cyclohexadiene-1,2-dicarboxylic acid, 5,6,7,8-tetrabromo1,3-cyclooctadiene, 2-cyclohexyl-1,3-butadiene, 2-methylene-3-butenoic acid and 2,4-pentadienenitrile. Presently preferred conjugated diolefins are those containing only carbon and hydrogen, since they are more readily available and less expensive. Especially preferred for use in the present invention are 1,3-butadiene and isoprene, because of availability and reactivity considerations.

CARBOXYLIC ACIDS

Organic Acid Reactant

The organic acid reactants employed in the process of my invention are the broad classes of mono and di-carboxylic acids optionally with their corresponding anhydrides, and include aliphatic as well as aromatic carboxylic acids. These carboxylic acids form the ester moiety in the final olefinic product in the process of my invention. These carboxylic acids of the monocarboxylic acids also can be represented by the general formula $$R''-CO_2H,$$ (III)

and the dicarboxylic acids can be represented by the general formula:

$$R'''(CO_2H)_2$$ (IV)

In the formulae indicated above, R" represents an alkyl, cycloalkyl, aryl, or combination radical such as alkaryl, aralkyl, cycloalkylaryl, and the like, as well as a variety of substituted derivatives thereof including halogen, cyano, —COOR', wherein the radicals can contain up to such as 4 substituents of halogen, cyano, -COOR' substituents.

R''' represents a valence bond, or alkylene, cycloalkylene, arylene, or combination radical such as alkarylene, cycloalkylarylene, aralkylene, and the like, and which radicals further can contain a variety of substituents as described for R" above, since such substituents are essentially inert to the conditions and reactants employed in the process of my invention. R' is as defined hereinabove.

Exemplary carboxylic acids include such as acetic acid, propanoic acid, butanoic acid, pentanoic acid, hexanoic acid, octanoic acid, dodecanoic acid, octadecanoic cid, cyclopentanecarboxylic acid, cyclohexanecarboxylic acid, benzoic acid, chloroacetic acid, cyanoacetic acid, trichloroacetic acid, 2-bromododecanoic acid, 2-ethylhexanoic acid, oxalic acid, succinic acid, adipic acid, terephthalic acid, 2-bromobutanoic acid, ethyl hydrogen adipate, 4-chlorobenzoic acid, 4-cyanobenzoic acid, 2,3,4,5-tetrachlorobenzoic acid and ethyl hydrogen-o-phthalate, and the like, or their corresponding anhydrides. Acetic acid is a presently preferred carboxylic acid species for use according to the process of this invention, because it is readily available, inexpensive, reactive, and easily handled. It is presently preferred that the carboxylic acid employed be one that is characterized as normally liquid for convenience in handling under the conditions of the reaction.

PRODUCTS

The general formulae shown below represent products obtained from the reaction of monocarboxylic acids of general formulae (III) or (IV) with an acyclic conjugated diene of general formula (I) or cyclic conjugated diene of general formula (II).

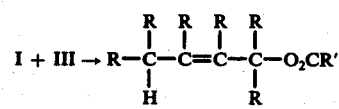

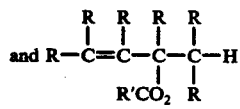

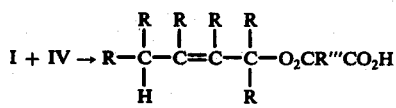

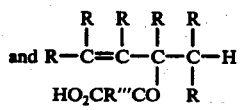

(V)

(VI)

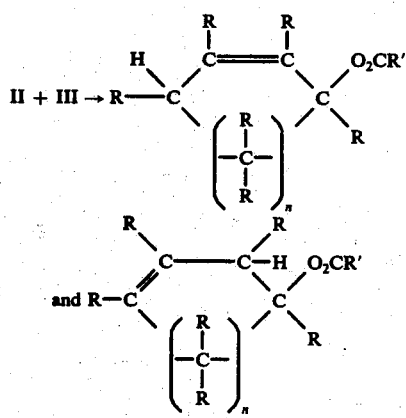

(VII)

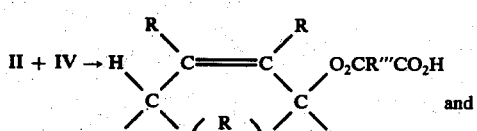

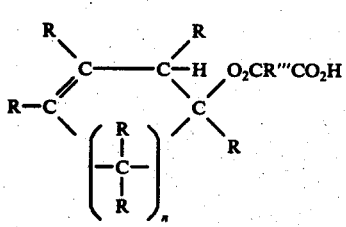

(VIII)

For simplicity, only two formulas are shown to illustrate the 1,4- and 1,2-modes of addition of the acid to the diene for each combination. It will be recognized however by those skilled in the art that the number of isomeric compounds expected from a given combination of diene and carboxylic acid may be greater than 2 if the conjugated diene is not symmetrical with respect to the conjugated double bonds and/or if Markownikoff's rule is not applicable. This fact is illustrated in the following:

Reaction of 2-methyl-1,3-butadiene with butanoic acid

The expected products from this combination are as follows:
  2-methyl-2-butenyl butanoate
  3-methyl-2-butenyl butanoate
  2-methyl-3-buten-2-yl butanoate
  3-methyl-3-buten-2-yl butanoate Reaction of 1,3-cyclohexadiene with benzoic acid Products expected from this combination are as follows:
  cyclohexen-3-yl benzoate
  cyclohexen-4-yl benzoate Reaction of 1,3-pentadiene with succinic acid The reaction of the above combination is expected to produce the following compounds:
  3-penten-2-yl hydrogen succinate
  2-pentenyl hydrogen succinate
  4-penten-2-yl hydrogen succinate
  1-penten-3-yl hydrogen succinate Reaction of 5-methyl-1,3-cyclohexadiene with terephthalic acid The products expected from this combination are as follows:
  4-methylcyclohexen-3-yl hydrogen terephthalate
  5-methylcyclohexen-3-yl hydrogen terephthalate
  5-methylcyclohexen-4-yl hydrogen terephthalate
  6-methylcyclohexen-4-yl hydrogen terephthalate
  6-methylcyclohexen-3-yl hydrogen terephthalate It can be seen from the above examples that the number of expected compounds from a given combination of conjugated diene and organic acid can range from 2 up to as many as 5 isomeric compounds.

CATALYSTS

The reaction according to the process of my invention is conducted employing a catalyst system which comprises a copper ion, an alkali metal ion, and a halide ion. The copper ion can be either cuprous or cupric. The alkali metal ion can be lithium, sodium, potassium, rubidium, or cesium, though lithium presently is preferred because the lithium compounds are generally more soluble than the other alkali metal compounds. The halide ion can be chloride, bromide, or iodide. It will be readily apparent, of course, that the halide component can be supplied at least in part by copper halides, alkali metal halides, or by a separate halide source.

Any copper compound can be used that provides a source of copper ion, including such as any of the halides, oxides, carbonates, carboxylates of such as up to 18 carbon atoms per molecule, nitrates, orthophosphates, sulfates, and the like, alone, or in admixture. Exemplary copper compounds include such as copper(II) acetate, copper(I) bromide, copper(II) bromide, copper(II) benzoate, copper(II) butanoate, copper(I)

chloride, copper(II) chloride, copper(II) dodecanoate, copper(II) octadecanoate, copper(I) oxide, copper(II) oxide, copper(II) salicylate, copper(I) iodide, copper(I) carbonate, copper(I) sulfate, copper(II) sulfate, copper(II) nitrate, copper(II) orthophosphate, and the like, alone or in admixture.

Any suitable alkali metal compound can be employed as a catalyst component in the process of my invention so long as it provides a source of alkali metal ion, including such as the halides, oxides, hydroxides, carbonates, carboxylates, nitrates, orthophosphates, sulfates, and the like, alone or in admixture similarly as described for the copper ion source. Typically such alkali metal source compounds include such as lithium chloride, lithium bromide, lithium iodide, lithium nitrate, lithium acetate, lithium bexzoate, lithium hydroxide, lithium oxide, lithium orthophosphate, lithium octadecanoate, lithium sodium, sodium chloride, sodium bromide, sodium acetate, sodium nitrate, sodium sulfate, potassium chloride, potassium acetate, potassium nitrate, potassium benzoate, potassium sulfate, rubidium chloride, rubidium nitrate, rubidium bromide, rubidium acetate, rubidium sulfate, cesium chloride, cesium acetate, cesium nitrate, cesium sulfate, cesium oxide, and the like, alone or in admixture.

My catalyst system includes a halide ion, which can be chloride, bromide, or iodide, or mixture. The halide-supplying compound employed can be the copper compound itself, or the alkali metal compound, or both. Other halide source compounds can be employed such as alkaline earth metal halides, or even other halides whose cation is substantially inert in the reaction conditions of my invention, particularly such as the ammonium halides.

In the catalyst system utilized according to my process, an appropriate exemplary molar ratio of alkali metal:copper employed broadly can be in the range of about 0.1:1 to 100:1, and preferably about 1:1 to 5:1 for best catalyt effectiveness, though the broad range should be considered exemplary and not as limitative, since the process is operable outside of the range. The ratio of halide ion:copper employed in the catalyst system of my invention also presently for exemplary purposes should be in the range of about 0.1:1 to 100:1, presently preferably about 1:1 to 5:1 for best catalyst effectiveness, though the broad range should be considered exemplary and not as limitative since the process is operable outside of the range.

My reaction can be and presently preferably carried out in the liquid phase with all reactants and catalyst compounds substantially in the liquid phase. Alternatively, if desired, the catalyst system of my invention can be dispersed in or on a suitable support material such as silica, crystalline zeolites, diatomaceous earth, and the like, particularly for use in the process carried out with the reactants in the vapor phase. Presently I prefer the liquid phase and my examples are directed toward this aspect, since milder conditions, e.g., lower reaction temperatures, can be utilized thereby tending to reduce the amounts of by products formed.

The catalyst concentration employed according to the process of my invention can be conveniently expressed in terms of the amount of copper employed relative to the amount of conjugated diolefin charged. Broadly, a suitable and exemplary ratio can range from about 0.1 mol percent up to an equimolar amount, presently preferably about 1 to 50 mol percent of copper based on the conjugated diolefin charged to the system, because of considerations of cost and efficiency. This ratio preferably is employed whether the process is carried out in the liquid or vapor phase.

REACTION CONDITIONS

The process is conducted in the absence of oxygen. Procedures for such exclusion of oxygen are known to those skilled in the process art. For example, the reactor means can be evacuated prior to charging the reactants, which reactants preferably have been degassed or otherwise treated to render them substantially oxygen-free. Alternatively, the reactor means can be charged with some or all of the reactants, and then purged briefly with an inert gas, such as nitrogen, to remove any oxygen or oxygen-containing gases therefrom. It should be noted that the reaction of my invention does not require the rigorous exclusion of traces of oxygen in order to accomplish the desired result, but the reaction is to be conducted with the substantial exclusion of oxygen. If oxygen is not substantially excluded, but rather if substantial oxygen does involve itself in the reaction, then the end products differ radically, resulting, for example, in carboxylate esters of butenediol by reaction of acetic acid with butadiene, rather than the desired product according to my reaction of carboxylate esters of butenol.

Temperatures employed for the process of my invention range widely, so long as sufficient heat is employed to provide effective reaction rates. Presently exemplary temperatures are suggested between about $+30°$ C and $250°$ C, more preferably presently about $100°$ C to $175°$ C because of considerations of balancing of reaction rate and selectivity for the desired products.

The pressure employed in the process can be that produced by the reactions themselves depending on the temperatures employed, for example, autogenous pressures ranging from about 50 to 150 psig. The process of my invention can be carried out in the liquid or vapor phase. Where liquid phase systems are utilized, it is convenient to employ an inert gas such as nitrogen, or helium, so as to maintain pressure such as about 500 to 1000 psig above the autogeneous pressure as an aid in maintaining the conjugated diolefin in the liquid phase and to assure exclusion of extraneous oxygen or air.

It is convenient to employ the organic acid reactant in large excess to serve as both reactant and reaction diluent for the process of this invention. Broadly, the amount of acid employed can be from an equimolar amount based on the conjugated diene up to a molar ratio of about 500/1. Preferably, the molar ratio of acid to conjugated diene is from about 2/1 up to about 10/1.

With regard to the use of normally solid acids in the instant invention, e.g., those which melt at temperatures above room temperature or thereabouts, such acids can be employed either in a molten state or in essentially solid state at the initial stages of the reaction. As more product forms (normally liquid materials), such products function as solvents for any undissolved acid reactant and thereby promote dissolution of the acid in the reaction mixture. Furthermore, the presence of the conjugated diene with those acids that are normally solids also exerts a solubilizing effect on the solid acids and thus promotes a fluid mixture for the reaction system. In the use of vapor phase in the process of using solid acids, such acids can be vaporized prior to charging to the reaction zone alone or in admixture with vaporized conjugated diene.

Time employed in the process is not critical, and can range widely, generally depending on the desired degree of conversion of the starting conjugated diolefin. Exemplary reaction times can range between such as less than 1 hour to over 18 hours, employing a batch process. It is within the scope of this invention to employ continuous process, liquid phase or vapor phase, and where a continuous process a supported catalyst as mentioned hereinbefore is preferred, employing recycle of unreacted conjugated diolefin and carboxylic acid to the reaction zone.

Since water present in the reaction mixture can hydrolyze the ester products of the reaction and thereby complicate product separation and reaction mixture workup, it is desirable to maintain an essentially anhydrous reaction system. One convenient way to assure this condition is to employ in admixture with the organic acid the corresponding anhydride of said acid. Any water present then would react with the anhydride to provide more organic acid and thereby consume the water. The use of the anhydride according to the above is an optional feature of the instant invention and the amount of anhydride employed can vary widely though generally it will be in the amount of 0.01 moles of anhydride up to 5 moles per mole of organic acic employed.

The monoolefinic esters, carboxylic acid esters of monoolefinic alcohols, produced by the process of my invention wherein a carboxylic acid is reacted with a conjugated diolefin, can be recovered from the resulting reaction mixture, either liquid or vapor phase, by any convenient recovery procedure. Typically, the reaction mixture can be distilled directly from the catalyst system, and products recovered as a distillate which can be further fractionally distilled for recovery of the monoolefinic ester. Or, the catalyst can be precipitated from the liquid phase system by employment of an inert nonpolar solvent such as n-hexane, and the catalyst then filtered for removal, and the filtrate then distilled for the recovery of the desired product. From vapor phase processes, the reaction zone effluent can be condensed, fractionally distilled for recovery of the product, while separated unreacted conjugated diolefin and carboxylic acid can be readily recycled to the reaction zone.

EXAMPLES

Examples provided herein are designed for a further understanding of my invention, to assist those skilled in the art to which the invention most nearly appertains. Particular species employed, of reactants, and catalyst components, as well as particular conditions employed, should be considered as exemplary, not as limitative of the scope of my invention as herein disclosed in my overall specification.

EXAMPLE I

A series of runs was carried out employing a 250 ml Fisher-Porter aerosol compatibility bottle as the reaction vessel. The vessel was equipped with a magnetic stirrer and was capable of being immersed in a heated oil bath to provide the heat for the reaction mixture. In each run, the reaction vessel was charged with the indicated amount of catalyst components shown in Table I below, 50 ml of acetic acid, 25 ml of acetic anhydride, and the indicated amount of butadiene charged from the vapor phase. The reaction mixture was placed in said oil bath and heated at about 140° C for 5 – 7 hrs. The reactor was usually vented while warming through a dry ice/acetone trap to recover unreacted butadiene. The reaction mixture then was cooled to about room temperature, mixed with ether, filtered, washed with water, washed with a sodium carbonate solution, then dried over magnesium sulfate and filtered before a final distillation to remove the ether dilluent. The distillation residue following removal of the ether was analyzed by gas-liquid phase chromatography to determide the amounts of the various components present. The catalytic components for this series of runs and the results obtained are summarized in Table I shown below.

Table I

| Run No. | Cu Compd (mmol.) | | Li Salt (mmol.) | Bd[a] mmol. | Esters[b] mmol. | Yield[c] % |
|---|---|---|---|---|---|---|
| 1 | Cu(OAc)$_2$ | (48) | Br$^-$(75) | 248 (131) | 19 | 8 (15)[f] |
| 2 | Cu$_2$Cl$_2$ | (48) | Cl$^-$(75) | 194 (185) | 85 | 44 (46)[g] |
| 3 | Cu$_2$O | (24) | Br$^-$(75) | 276 (158) | 27 | 10 (17)[h] |
| 4 | CuI | (12) | I$^-$(38) | 204 (176) | 59 | 29 (34)[i] |
| 5 | Cu$_2$Cl$_2$ | (48) | 0 | 215 (94) | 2 | 1 (2) |
| 6 | Cu$_2$(OAc)$_2$ | (24) | OA$^-$(75) | 222 (—)[d] | 13 | 6 (—) |
| 7 | Cu$_2$(OAc)$_2$ | (24) | 0 | 222 (—) | 15 | 7 (—) |
| 8[e] | Cu$_2$Cl$_2$ | (48) | Cl$^-$(75) | 472 (88) | 0 | 0 |

[a]Bd = 1,3-butadiene. The number in parenthesis indicates the amount (mmole) reacted and the first number the amount charged.
[b]Mixture of the acetate esters of 3-buten-2-ol and 2-buten-1-ol.
[c]The number in parenthesis indicates the ester yield calculated based on the amount of butadiene reacted. The first number indicates the yield of ester based on the amount of butadiene charged.
[d]The symbol (—) indicates not determined.
[e]This run was conducted at room temperature, about 25° C.
[f]An 8% yield of VCH based on the butadiene reacted was also obtained.
[h]A 25% yield of VCH based on the butadiene reacted was also obtaind.
[i]Only a trace of VCH was observed in the product mixture.

In Runs of the invention 1, 2, 3, 4, and 8, the halide source at least in part was from the lithium. In Runs, 2, 4, and 8, additional halide was supplied by the copper salt employed.

In Run 5, no lithium component was employed, and yield of esters was negligible.

In Control Run 6, no halide ion was available, and yield of esters was relatively low. In Run 1, the anomalous apparent low ester yield is believed attributable to loss of product in handling the reaction mixture.

In Run 7, no lithium salt, and no halide ion, were employed, and the yield of esters was relatively low.

In Run 8, while the catalyst system was present and all reactants were present, the reaction rate was substantially zero, since the run was conducted at room temperature, about 25° C, and this was too low for effective reaction rates.

Runs 1, 2, 3, and 4, all of the invention, and at suitable reaction temperatures, produce good yields of desired product. Esters calculated are the mixture of acetate ester 3-buten-2-ol and 2-buten-1-ol. Esters of 3-buten-1-ol do not appear when butadiene is reacted with acetic acid under the conditions of this invention since acetic acid can add to the conjugated diene either in a 1,4- or a 1,2-fashion, and the addition in the 1,2-mode follows Markownikoff's rule for addition to olefinic systems.

EXAMPLE II

A further run was conducted in the same manner as those of Example I, but in which an additional quantity of butadiene was charged to the reaction vessel after the initial 6-hour reaction at 140° C. In this run, the reaction vessel was charged with 5.0 grams (37.5 mmoles) of lithium iodide, 2.3 grams (12 mmoles) of cuprous iodide, 50 ml of acetic acid, 25 ml of acetic anhydride, and 12.2 grams (226 moles) of butadiene charged from the vapor phase. This reaction mixture was heated for 6 hours at 140° C while the autogeneous pressure decreased from 112 to 65 psig. The reaction vessel then was charged with an additional 12.8 grams (237 mmoles) of butadiene and heated for 6 hours at 140° C while the pressure on the vessel decreased from 130 to 105 psig. At the end of the reaction period, the unreacted butadiene was distilled into a dry ice/acetone trap and 9.0 grams was recovered therein. The reaction mixture was mixed with ether, washed with water, and the ether phase neutralized with sodium carbonate solution. The ether phase was dried over magnesium sulfate and filtered prior to distillation of the ether from the reaction mixture. The distillation residue weighed 28.2 grams. The residue was analyzed by gas-liquid phase chromatography which indicated that there were obtained 48.2 mmoles of the acetate ester of 3-buten-2-ol and 70.5 mmoles of the acetate ester of 2-buten-1-ol for a yield of 26% of esters based on the butadiene charged and a yield of 40% based on the amount of butadiene converted. The analysis showed that that this run also gave 3.27 grams or 30.3 mmoles of 4-vinylcyclohexene for a 15% yield of this compound based on the amount of butadiene converted. The tendency for the conjugated diene to cyclodimerize is less for conjugated dienes above butadiene, and therefore this side reaction would probably be less of a problem for these dienes than in the case of butadiene.

EXAMPLE III

A further run was conducted according to the invention employing a one liter autoclave as the reaction vessel. In this run, the autoclave was charged with 9.6 grams (96 mmoles) of cuprous chloride, 6.4 grams (150 mmoles) of lithium chloride, 200 ml of acetic acid, 50 ml of acetic anhydride, and 56 grams (1.037 moles) of butadiene charged from the vapor phase. The reaction mixture was heated with stirring at 140° C for 17 hours. At the end of the reaction period, the autoclave was cooled, vented and opened. The reaction mixture was taken up in ether, washed with water, and then with sodium carbonate solution. The ether solution was dried over magnesium sulfate and then filtered prior to distillation of the reaction mixture to remove the ether. The distillation residue weighed 64 grams and was analyzed by gas-liquid phase chromatography. The analysis disclosed 175 mmoles of the acetate ester of 3-buten-2-ol and 106 mmoles of the acetate ester of 2-buten-1-ol for a yield of 27% of the esters based on the butadiene charged.

EXAMPLE IV

Another run was carried out according to the invention in which triphenylphosphine was employed as a catalyst adjuvant. In this run, a 250 ml Fisher-Porter aerosol compatibility bottle equipped with a magnetic stirrer as charged with 2.4 grams (24 mmoles) of cuprous chloride, 3.2 grams (75 mmoles) of lithium chloride, 6.3 grams (24 mmoles) of triphenylphosphine, 50 ml of acetic acid, 25 ml of acetic anhydride, and 12.8 grams (237 mmoles) of butadiene charged from the vapor phase. The reaction mixture was heated for 5 hours at 140° C while the autogenous pressure decreased from 122 to 95 psig. The cooled reaction mixture was vented into a dry ice/acetone trap while warming to 60° C to recover unreacted butadiene. There was recovered in the dry ice/acetone trap 5.3 grams of unreacted butadiene. The remaining reaction mixture was taken up in ether, washed with water, the ether solution neutralized with sodium carbonate, dried over magnesium sulfate and filtered. The mixture then was distilled to remove the ether and the distillation residue which weighed 9.3 grams was analyzed by gas-liquid phase chromatography. The analysis disclosed 2.9 grams (25.5 mmoles) of the acetate ester of 3-butene-2-ol and 4.45 grams (39.0 mmoles) of the acetate ester 2-buten-1-ol for a total yield of 64.5 mmoles of the esters. This represents a yield of 27% based on the butadiene charged or a yield of 46% based on the butadiene converted. The analysis also showed that there was obtained 1.15 grams or 10.6 mmoles of 4-vinylcyclohexene for a yield of 15% of this compound based on the butadiene converted. The results appear to indicate that the presence of the triphenylphosphine had no significant effect on the yield of the olefinic esters over all or upon the selectivity of the reaction.

EXAMPLE V

In a control run, a 250 ml Fisher-Porter aerosol compatibility bottle equipped with a magnetic stirrer was charged with 8 grams (48 mmoles) of silver acetate, 75 ml of acetic acid and 11.1 grams (206 mmoles) butadiene charged from the vapor phase. The reaction mixture was heated for 6 hours at 140° C and there was observed essentially no pressure drop on the reaction vessel. At the end of the reaction period, the reaction mixture was vented and the product mixture was discarded since apparently no reaction had occurred.

EXAMPLE VI

Another control run was conducted in which a 250 ml Fisher-Porter aerosol compatibility bottle equipped with a magnetic stirrer was charged with 4.8 grams (48 mmoles) of cuprous chloride, 3.2 grams (75 mmoles) of lithium chloride, 50 ml of acetic acid, 25 ml of acetic anhydride, and 16.2 grams (145 mmoles) of dry 1-octene. The reaction mixture was heated at 140° C for 5 hours. The reaction miture was then taken up in ether, washed with water and the ether solution washed with sodium carbonate until neutral, then dried over magnesium sulfate and filtered. The ether was removed from the reaction mixture by fractional distillation. The distillation residue which weighed 16.8 grams, was analyzed by gas-liquid phase chromatography. The analysis showed that only about 12 mmoles of the 1-octene had reacted and that about 0.6 gram of two unidentified materials was obtained as the reaction product. This result indicates the very low reactivity of 1-olefins in the reaction system of the instant invention.

EXAMPLE VII

Another control run was carried out in which the same type of reaction vessel employed in Example VI was charged with 4.8 grams (48 mmoles) of cuprous chloride, 3.2 grams (75 mmoles) of lithium chloride, 50 ml of freshly distilled solfolane, 10 ml (12.9 grams, 215 mmoles) of acetic acid, 1.0 ml of acetic anahydride and 12 grams (222 mmoles) of butadiene charged from the vapor phase. The reaction vessel was heated for 6.5 hours at 100° C while the pressure on the reaction vessel decreased from 139 to 130 psig. There was recovered in a dry ice/acetone trap 11 grams of unreacted butadiene which indicated that the conversion was less tha 10%. The reaction mixture was, therefore, discarded. This result indicates that the polar solvent, sulfolane (tetrahydrothiophene-1,1dioxide), was unsuited for the reaction system of the instant invention.

EXAMPLE VIII

Another control run was carried out employing the same type of reaction vessel as that employed in Example VI. In this run, the reaction vessel was charged with 75 ml of acetic acid, 1 ml of sulfuric acid, and 11.7 grams (217 mmoles) of butadiene charged from the vapor phase. The reaction vessel was placed in an oil bath and heated at 140° C for about 3 hours. At the end of the reaction period, the reaction mixture was taken up in ether, washed with water, and the ether solution washed with sodium carbonate, then dried over magnesium sulfate, filtered and the ether distilled away. The distillation residue weighed 19.1 grams and gas-liquid phase chromatography analysis showed the presence of very small amounts of the acetete esters of 3-buten-2-ol and 2-buten-1-ol with no indication of 4-vinylcyclohexene. In addition, the reaction mixture was quite dark in color. No further analysis or separation of the reaction mixture was attempted. This run demonstrates the poor results obtained using a strong acid catalyst in an attempt to prepare esters of the butenols by reaction of the carboxylic acid with butadiene.

EXAMPLE IX

A run was conducted in which a 250 ml Fisher-Porter aerosol compatibility bottle equipped with a magnetic stirrer was charged with 4.6 grams (21.5 mmoles) of 1,4-dibromo-2-butene, 6.5 grams (75 mmoles) of lithium bromide, 9.6 grams (48 mmoles) of cupric acetate monohydrate, 25 ml of acetic anhydride, 50 ml of acetic acid and 10.7 grams (198 mmoles) of butadiene charged from the vapor phase. The reaction vessel was placed in an oil bath and heated at 140° C for 6 hours while the autogenous pressure decreased from 100 to 48 psig. The cooled reaction vessel was vented through a dry ice-/acetone trap while warming the mixture of reactants to 60° C. No butadiene was recovered in the trap. The reaction mixture was then cooled, diluted with ether, filtered, and the ether solution washed with water, sodium carbonate solution and then dried over magnesium sulfate and filtered once again. The ether was distilled away from the reaction mixture. The distillation residue following removal of the ether was further fractionally distilled through an 18 inch Vigreaux column. Three fractions were obtained in this distillation. Each fraction was analyzed by gas-liquid phase chromatography which revealed that there was obtained 3.17 grams (27.8 mmoles) of the acetate ester of 3-buten-2-ol and 4.15 grams (36.2 mmoles) of the acetate ester of 2-buten-1-ol for a combined yield of 7.32 grams (64 mmoles) of the esters. This represents a yield of 32% based on the butadiene charged. There was also obtained in this run 1.98 grams of 1,2-diacetoxy-3-butene and 3.32 grams of 1,4-diacetoxy-2-butene for a total yield of 31 mmoles of these diesters. This amount represents a yield of 16% of the diesters based on the butadiene charged. At least a major portion of the diacetoxybutenes is believed to have arisen from the presence of the 1,4-dibromo-2-butene in the reaction mixture.

EXAMPLE X

Another control run was conducted in which a 250 ml Fisher-Porter aerosol compatibility bottle equipped with a magnetic stirrer was charged with 0.18 grams (1 mmole) of palladium (II) chloride, 75 ml of chloroform, 25 ml of acetic acid, 3.1 grams (10 mmoles) of triphenylphosphite, 0.8 grams (10 mmoles) of anhydrous sodium acetate, and 19.5 grams (361 mmoles) of butadiene charged from the vapor phase. The reaction mixture was heated at 100° C for 1 hour, then at 140° C for 2 hours. Very little decrease in the autogenous pressure was noted during the reaction period. At the end of the reaction, the reactor was cooled, then vented, while warming, into a dry ice/acetone trap to recover unreacted butadiene. There was recovered by this means 14.2 grams of unreacted butadiene. The reactor was opened and the reaction mixture filtered into a distillation flask. Gas-liquid phase chromatography analysis of the distillation residue showned that substantially no reaction had occurred between the butadiene and the acetic acid to form the esters of the butenols.

The unsaturated ester products of this invention can be employed as monomers in polymerization systems to give resins, plastics, and the like with pendant ester groups in the manner of allyl acetate or vinyl acetate containing polymers. Furthermore, the unsaturated esters can be hydrogenated to the saturated esters with conventional hydrogenation catalysts, and the product saturated esters can be employed in applications well known to the art such as solvents or vehicles in a variety of compositions.

The disclosure, including data, illustrate the value and effectiveness of my invention. The examples, the knowledge and background of the field of the invention and general principles of chemistry and other applicable sciences, have formed the basis from which the broad descriptions of the invention including the ranges of conditions and generic groups of operant component have been developed, which have formed the basis for my claims here appended.

I claim:

1. A process for the production of esters of monoolefinically unsaturated alcohols which comprises reacting a conjugated diolefin with an organic acid reactant under reaction conditions in the substantial absence of oxygen and employing catalytic amounts of a catalyst system consisting essentially of a copper ion, an alkali metal ion, and a halide,
wherein said conjugated diolefin is an acyclic conjugated diolefin represented by the formula

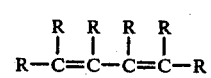 (I)

or a cyclic conjugated diolefin represented by the formula

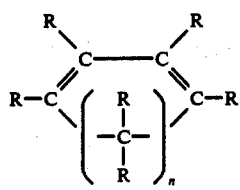
(II)

wherein each R is individually selected from hydrogen, halogen, cyano, —COOR', and the monovalent hydrocarbyl radicals, wherein R' is hydrogen, or alkyl or aryl hydrocarbon radical, and n has the value of 1 to 12, and wherein said organic acid reactant is a monocarboxylic acid R"COOH, a dicarboxylic acid R'"(COOH)$_2$, a corresponding anhydride, or both; wherein R" is an alkyl, cycloalkyl, aryl, or combination radical, or the halogen, cyano, or —COOR' derivative thereof, wherein the R" radical can contain up to 4 such substituents; wherein said R'" is a valence bond, or an alkylene, cycloalkylene, arylene, or combination radical, wherein R'" further can contain up to 4 substituents selected from the group consisting of halogen, cyano, and —COOR', and employing a catalyst concentration expressed in terms of the amount of copper ion:conjugated diolefin charged in the range of about 0.01 mol percent up to an equimolar amount.

2. The process according to claim 1 wherein said acyclic conjugated diolefin contains 4 to 16 carbon atoms per molecule, and said cyclic conjugated diolefins contain 5 to 16 carbon atoms per molecule, such that the total number of carbon atoms in all R substituents does not exceed 12.

3. The process according to claim 2 wherein said conjugated diolefin is a said acyclic conjugated diolefin and is selected from the group consisting of 1,3-butadiene, 2-methyl-1,3-butadiene, 2-chloro-1,3-butadiene, 2-ethyl-1,3-butadiene, 2-chloro-3-methyl-1,3-butadiene, 1,4-diphenyl-1,3-butadiene, 1,3-hexadiene, 1,3-pentadiene, 1,3-octadiene, 2-cyano-1,3-butadiene, 2-carbethoxy-1,3-butadiene, 2-cyclohexyl-1,3-butadiene, 2-methylene-3-butenoic acid, and 2,4-pentadienenitrile.

4. The process according to claim 2 wherein said conjugated diolefin is a said cyclic conjugated diolefin and is selected from the group consisting of 1,3-cyclohexadiene, 1,3-cyclooctadiene, 1,3-cyclododecadiene, cyclopentadiene, 5-methyl-1,3-cyclohexadiene, 2,4-cyclohexadiene-1,2-dicarboxylic acid, and 5,6,7,8-tetrabromo-1,3-cyclooctadiene.

5. The process according to claim 4 wherein said organic acid reactant is said monocarboxylic acid, or said monocarboxylic acid plus the corresponding anhydride, said monocarboxylic acid contains up to 18 carbon atoms per molecule, and is selected from the group consisting of acetic acid, propanoic acid, butanoic acid, pentanoic acid, hexanoic acid, octanoic acid, dodecanoic acid, octadecanoic acid, cyclopentanecarboxylic acid, cyclohexanecarboxylic acid, benzoic acid, chloroacetic acid, cyanoacetic acid, trichloroacetic acid, 2-bromododecanoic acid, 2-ethylhexanoic acid, 2-bromobutanoic acid, ethyl hydrogen adipate, 4-chlorobenzoic acid, 4-cyanobenzoic acid, 2,3,4,5-tetrachlorobenzoic acid, and ethyl hydrogen-o-phthalate.

6. The process according to claim 2 wherein said organic acid reactant is said dicarboxylic acid, said dicarboxylic acid contains up to 18 carbon atoms per molecule, and is selected from the group consisting of oxalic acid, succinic acid, hexanedioic acid, and terephthalic acid.

7. The process according to claim 1 wherein said copper ion is cuprous or cupric, and is supplied by a copper compound selected from the group consisting of copper halides, oxides, hydroxides, nitrates, carbonates, sulfates, orthophosphates, and hydrocarbon carboxylates.

8. The process according to claim 7 wherein said copper compound is selected from the group consisting of copper acetate, copper bromide, copper benzoate, copper butanoate, copper chloride, copper dodecanoate, copper octadecanoate, copper sulfate, copper nitrate, copper orthophosphate, copper oxide, copper salicylate, copper iodide, and copper carbonate, and wherein said copper in said copper compound is chosen from the group consisting of cuprous and cupric.

9. The process according to claim 1 wherein said alkali metal ion is selected from the group consisting of lithium, sodium, potassium, rubidium, and cesium, and said alkali metal ion is supplied by an alkali metal compound selected from the group consisting of alkali metal halides, oxides, hydroxides, hydrocarbon carboxylates, nitrates, sulfates, and orthophosphates.

10. The process according to claim 9 wherein said alkali metal compound is selected from the group consisting of lithium chloride, lithium bromide, lithium iodide, lithium nitrate, lithium hydroxide, lithium orthophosphate, lithium acetate, lithium benzoate, lithium oxide, lithium sulfate, lithium octadecanoate, sodium chloride, sodium nitrate, sodium bromide, sodium sulfate, sodium acetate, potassium chloride, potassium nitrate, potassium acetate, potassium sulfate, potassium benzoate, rubidium nitrate, rubidium chloride, rubidium sulfate, rubidium bromide, rubidium acetate, cessium nitrate, cesium chloride, cesiium acetate, cesium sulfate, and cesium oxide.

11. The process according to claim 1 wherein said halide is a chloride, bromide, or iodide, supplied by a halide providing compound selected from the group consisting of cuprous or cupric halide, alkali metal halides, alkaline earth metal halides, ammonium halides, or mixtures.

12. The process according to claim 1 wherein said effective catalyst ratios are represented by a molar ratio of alkali metal ion:copper ion in the range of about 0.1:1 to 100:1, and a molar ratio of halide ion:copper ion in the range of about 0.1:1 to 100:1.

13. The process according to claim 12 wherein each of said ratios is in the range of about 1:1 to 5:1.

14. The process according to claim 12 employing a ratio of said organic acid reactant to said conjugated diene is in the molar range of about 1:1 to 500:1.

15. The process of claim 14 wherein said molar range is about 2:1 to 10:1.

16. The process according to claim 15 wherein the mol ratio of said copper ion:conjugated diolefin charged is in the range of about 1 to 50 mol percent.

17. The process according to claim 15 wherein said reaction conditions include a contacting temperature in the range of about 30° to 250° C.

18. The process according to claim 17 wherein said copper ion is supplied by cupric acetate, said alkali metal is lithium, said halide is bromide, said conjugated diene is butadiene, and said carboxylic acid is acetic acid, wherein said products comprise acetate esters of 3-buten-2-ol and 2-buten-1-ol.

19. The process according to claim 17 wherein said copper ion is supplied by cuprous chloride, said alkali metal ion is a lithium ion, said halide is chloride, said conjugated diene is butadiene, and said carboxylic acid is acetic acid, wherein said products comprise acetate esters of 3-buten-2-ol and 2-buten-1-ol 20. The process according to claim 17 wherein said copper ion is supplied by cuprous oxide, said alkali metal ion is a lithium ion, said halide is bromide, said conjugated diene is butadiene, and said carboxylic acid is acetic acid, wherein said products comprise acetate esters of 3-buten-2-ol and 2-buten-1-ol 21. The process according to claim 17 wherein said copper ion is supplied by cuprous iodide, said alkali metal ion is a lithium ion, said halide is iodide, said conjugated diene is butadiene, and said carboxylic acid is acetic acid, wherein said products comprise acetate esters of 3-buten-2-ol and 2-buten-1-ol.

22. The process of claim 1 wherein said catalyst system is a supported catalyst employing a support of silica, zeolite, or diatomaceous earth.

23. A process for the production of esters of monoolefinically unsaturated alcohols which comprises reacting a conjugated diolefin with an organic acid reactant under reaction conditions in the substantial absence of oxygen, and employing catalytic amounts of a catalyst system consisting essentially of a copper ion, an alkali metal ion, and a halide, wherein said conjugated diolefin is an acyclic conjugated diolefin represented by the formula $$R-\overset{R}{\underset{|}{C}}=\overset{R}{\underset{|}{C}}-\overset{R}{\underset{|}{C}}=\overset{R}{\underset{|}{C}}-R \quad (I)$$

or a cyclic conjugated diolefin represented by the formula

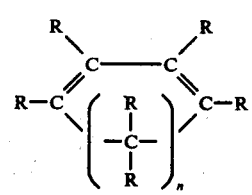

(II)

wherein each R is individually selected from hydrogen, halogen, cyano, —COOR', and the monovalent hydrocarbyl radicals, wherein R' is hydrogen, or an alkyl or aryl hydrocarbon radical of up to 10 carbon atoms, and n has the value of 1 to 12, wherein said organic acid reactant is a monocarboxylic acid R"COOH, a dicarboxylic acid R'"(COOH)$_2$, a corresponding anhydride, or both; wherein R" is an alkyl, cycloalkyl, aryl, or combination radical, or the halogen, cyano, or —COOR' derivative thereof, wherein the R" radical can contain up to 4 such substituents; wherein said R'" is a valence bond, or an alkylene, cycloalkylene, arylene, or combination radical wherein R'" further can contain up to 4 substitutents selected from the group consisting of halogen, cyano, and —COOR', wherein R' is hydrogen, alkyl, or aryl hydrocarbon radical of up to 10 carbon atoms, and wherein said reaction conditions include a contacting temperature in the range of about 30° C. to 250° C., and employing a catalyst concentration expressed in terms of the amount of copper ion:conjugated diolefin charge in the range of about 0.01 mol percent up to an equimolar amount.

* * * * *